(12) United States Patent
Zhang et al.

(10) Patent No.: US 7,786,336 B2
(45) Date of Patent: Aug. 31, 2010

(54) CATALYST COMPOSITION FOR ETHYLENE OLIGOMERIZATION AND THE USE THEREOF

(75) Inventors: Baojun Zhang, Beijing (CN); Tao Jiang, Beijing (CN); Jianzhong Li, Beijing (CN); Lihua Xing, Beijing (CN); Yingnan Ning, Beijing (CN); Shukun Sun, Beijing (CN); Dongting Kuang, Beijing (CN); Yongcheng Sun, Beijing (CN); Yunguang Han, Beijing (CN); Qian Chen, Beijing (CN); Hongxia Chen, Beijing (CN); Deshun Zhang, Beijing (CN); Yulong Li, Beijing (CN); Yongjun Zhang, Beijing (CN); Huimin Yuan, Beijing (CN); Sihan Wang, Beijing (CN); Guizhi Wang, Beijing (CN); Jingyuan Zhang, Beijing (CN)

(73) Assignee: Petrochina Company Limited, Beijing (CN)

( * ) Notice: Subject to any disclaimer, the term of this patent is extended or adjusted under 35 U.S.C. 154(b) by 761 days.

(21) Appl. No.: 11/716,540

(22) Filed: Mar. 9, 2007

(65) Prior Publication Data

US 2007/0232481 A1    Oct. 4, 2007

(30) Foreign Application Priority Data

Mar. 10, 2006    (CN) .................. 2006 1 0057254

(51) Int. Cl.
*C07C 2/26* (2006.01)
*C07C 2/32* (2006.01)
*B01J 31/14* (2006.01)
*B01J 31/18* (2006.01)
*B01J 31/22* (2006.01)

(52) U.S. Cl. .............. 585/513; 585/514; 585/520; 585/527; 502/103; 502/121; 502/123; 502/128

(58) Field of Classification Search .............. 585/513, 585/514, 520, 527; 502/103, 121, 123, 128
See application file for complete search history.

(56) References Cited

U.S. PATENT DOCUMENTS

| 3,635,937 | A | 1/1972 | Bauer et al. |
| 3,676,523 | A | 7/1972 | Mason |
| 3,906,053 | A | 9/1975 | Lanier |
| 6,184,428 | B1 | 2/2001 | Zahoor et al. |
| 2006/0229480 | A1* | 10/2006 | Blann et al. .................. 585/535 |

FOREIGN PATENT DOCUMENTS

EP    1443927    10/1962

| WO | WO 99/02472 | | 1/1999 |
| WO | WO 2004/056477 | * | 7/2004 |
| WO | WO 2004/056478 | | 7/2004 |

OTHER PUBLICATIONS

Brooke L. Small and Maurice Brookhart, *Iron-Based Catalysts with Exceptionally High Activities and Selectivities for Oligomerization of Ethylene to Linear α-Olefins*, pp. 7143-7144, 1998, J. Am. Chem. Soc., vol. 120, No. 28.

George J.P. Britovsek, Vernon C. Gibson, Brian S. Kimberley, Peter J. Maddox, Stuart J. McTavish, Gregory A. Solan, Andrew J.P. White and David J. Williams, *Novel Olefin polymerization Catalysts Based on Iron and Cobalt*, pp. 849-850, Chem. Commun., 1998.

\* cited by examiner

*Primary Examiner*—Caixia Lu
(74) *Attorney, Agent, or Firm*—Dority & Manning, P.A.

(57) ABSTRACT

The present invention relates to a catalyst composition for ethylene oligomerization and the use thereof. Such catalyst composition includes chromium compound, ligand containing P and N, activator and accelerator; wherein the chromium compound is selected from the group consisting of acetyl acetone chromium, THF-chromium chloride and Cr(2-ethylhecanoate)$_3$; general formula of the ligand containing P and N is shown as:

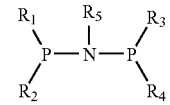

in which $R_1$, $R_2$, $R_3$ and $R_4$ are phenyl, benzyl, or naphthyl. $R_5$ is isopropyl, butyl, cyclopropyl, cyclopentyl, cyclohexyl or fluorenyl; the activatior is methyl aluminoxane, ethyl aluminoxane, propyl aluminoxane and/or butyl aluminoxane; the accelerator is selected from the group consisting of 1,1,2,2,-tetrachloroethane, 1,1,2,2-tetrabromoethane, 1,1,2,2-tetrafluoroethane, and compounds having a formula of $X_1R_6X_2$, in which $X_1$ and $X_2$ are F, Cl, Br, I or alkoxyl, $R_6$ is alkylene or arylene group; the molar ratio of chromium compound, ligand containing P and N, activator and accelerator is 1:0.5~10:50~3000:0.5~10. After mixing the four components mentioned previously under nitrogen atmosphere for 10 minutes, they are incorporated to the reactor, or these four components are incorporated directly into the reactor. Then ethylene is introduced for oligomerization. Such catalyst can be used in producing 1-octene through ethylene oligomerization. It is advantageous in high catalysing activity, high 1-octene selectivity, etc. The catalytic activity is more than $1.0 \times 10^6$ g product·ma$^{-1}$ Cr·h$^{-1}$, the fraction of $C_8$ linear α-olefin is more than 70% by mass.

8 Claims, No Drawings

CATALYST COMPOSITION FOR ETHYLENE OLIGOMERIZATION AND THE USE THEREOF

FIELD OF THE INVENTION

The present invention relates to a catalyst system, in particular to a catalyst composition for ethylene oligomerization and to the use thereof.

BACKGROUND OF THE INVENTION

As it is known that linear α-olefins, such as 1-octene, 1-hexene, etc, are important chemical products and intermediates, they are widely applied in various fields such as comonomers of polyethylene, alcohols plasticizers, flavor additives, synthetic lubricant and additives of oil products. Employing 1-octene and 1-hexene as comonomers will significantly improve the density, and mechanical properties such as tear strength and tensile strength of polyethylene. When be used as alcohols to produce plasticizers, they could endue polyethylene articles better softness at low temperature, processing behavior, better outdoor weathering durability, particularly suitable for wires and cables, automobile accessories, decoration materials, etc.

Even though 1-octene is of great importance in chemical industry, now there is no synthesis technique to produce 1-octene through ethylene oligomerization with high selectivity. In traditional process of ethylene oligomerization, the carbon number of the products is accordant with Schulz-Flory Distribution that results to a lower concentration of 1-octene in the oligomer products. For example, U.S. Pat. No. 6,184,428 discloses a kind of nickel catalyst using boron compound as cocatalyst, which could catalyze ethylene oligomerization to obtain the mixture of linear α-olefins, wherein the amount of 1-octene is 19%. SHOP process (U.S. Pat. Nos. 3,676,523 and 3,635,937) uses a similar catalyst system, and the amount of 1-octene reaches to 11% of oligomer products. Other typical ethylene oligomerization processes, such as Chevron process (DE 1,443,927) of Gulf Research Development Co., and ethylene oligomerization process (BP/Amoco, U.S. Pat. No. 3,906,053) of Ethyl Corp., generally produce 1-octene with concentration of about 13~25%. Chromium-based catalyst systems are mainly used in trimerization of ethylene, wherein the concentration of 1-octene is low (less than 3%). A iron-based catalyst reported recently (J. Am. Chem. Soc., 1998, 120:7143; Chem Commun. 1998,849; WO 99/02472) for ethylene oligomerization also results to oligomer products with wider distribution, in which the concentration of 1-octene is low (less than 20%) either. According to WO 2004/056478, tetramerization of ethylene produces 1-octene with concentration of no more than 69.3%.

SUMMARY OF THE INVENTION

The present invention is to provide a new catalyst composition, particularly the invention relates to a kind of catalyst composition for ethylene oligomerization. The composition includes chromium compound, ligand containing P and N, activators and accelerators, wherein the chromium compound is selected from the group consisting of acetyl acetone chromium, THF-chromium chloride and/or Cr(2-ethylhecanoate)$_3$.

The general formula of the Ligand containing P and N is shown as follow:

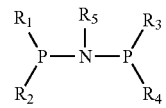

wherein $R_1$, $R_2$, $R_3$ and $R_4$ are phenyl, benzyl, fluorenyl or naphthyl. $R_5$ is isopropyl, butyl, cyclopropyl, cyclopentyl, cyclohexyl or fluorenyl;

The activator is methylaluminoxane, ethylaluminoxane, propylaluminoxane and/or butylaluminoxane.

The accelerator is selected from the group consisting of 1,1,2,2-tetrachloroethane, 1,1,2,2-tetrabromoethane, 1,1,2,2,-tetrafluoroethane, and compounds having a formula of $X_1R_6X_2$, in which $X_1$ and $X_2$ are F, Cl, Br, I or alkoxyl, $R_6$ is alkylene or arylene group.

The molar ratio of the chromium compound:the ligand containing P and N:the activator:the accelerator is 1:0.5~10:50~3000:0.5~10.

In one aspect of the invention, four components, i.e. chromium compound, ligand containing P and N, activator and accelerator, can be mixed under nitrogen atmosphere for at least 10 minutes before being added to a reactor, then ethylene is introduced for oligomerization. In another embodiment of the invention, the four components, i.e., the chromium compound, the ligand containing P and N, the activator and the accelerator are added directly to the reactor respectively, then ethylene is introduced for oligomerization. The reaction temperature is between 30° C. and 200° C., preferably between 30° C. and 90° C., more preferably between 30° C. and 70° C. The reaction pressure is between 0.5 MPa and 20.0 MPa, preferably between 1 MPa and 10 MPa, more preferably between 2 MPa and 6 MPa. The reaction time is between 0.1 hour and 2 hours, preferably between 0.3 hour and 1 hour, more preferably between 0.5 hour and 0.7 hour.

The present invention also relates to a preparation process of catalyst composition useful for ethylene oligomerization. The process includes sequentially mixing and reacting the activator, the Ligand containing P and N, the chromium compound and the accelerator in inert solvent under nitrogen atmosphere, wherein the molar ratio of the chromium compound:the ligand containing P and N:the activator:the accelerator is 1:0.5~10:50~3000:0.5~10. Preferably the inert solvent includes cyclohexane, xylene or isopropylbenzene.

The ethylene oligomerization mainly carries out in inert solvent. A suitable solvent can be selected from the group consisting of alkanes, arenes, halohydrocarbons or alkenes. The typical solvent is, but not limited to, benzene, toluene, xylene, isopropylbenzene, n-heptane, n-hexane, methyl cyclohexane, cyclohexane, 1-hexene, 1-octene, ionic liquid, etc.

The chief advantages and effects of the present invention lie in chromium-based catalyst of the invention because of the action of the accelerator, it is easily for four ethylene molecules to coordinate on four coordination bonds of chromium atom that are perpendicularly to each other. It is thus advantageous for self-polymerization of the four ethylene molecules to produce 1-octene selectively. Therefore, the catalyst has advantages of high activity, good selectivity to producing 1-octene and less by-product of polyethylene. The catalyst has activity of more than $1.0 \times 10^6$ g product·mol$^{-1}$ Cr·h$^{-1}$, while fraction of $C_8$ linear α-alkene is more than 70% by mass.

DETAILED DESCRIPTION OF PREFERRED EMBODIMENTS

EXAMPLE 1

1. Preparation of (diphenyl)phosphorous-nitrogen(cyclopropyl)phosphorous(diphenyl) ligand Dehydrated dichloromethane (20 mL), triethylamine (3.75 mL) and diphenyl phosphorus chloride (1.326 mL, 7.2 mmol) were added to a 100 mL reactor equipped with agitator and substituted with $N_2$ completely. The temperature was reduced to 0° C. Cyclopropylamine (3.6 mmol) was added gradually. The reaction system was agitated for 30 min, then heated to room temperature to keep reaction for another 12 hours. The product was obtained by filtering and drying (0.87 g, 56.6%).

2. Preparation of the Catalyst

Dehydrated toluene (10 mL) was added to a 100 mL reactor equipped with agitator and substituted with $N_2$ completely. Then 1.4 mol/L of solution of methylaluminoxane in toluene (c), (diphenyl)phosphorous-nitrogen(cyclopropyl)phosphorous(diphenyl) ligand (b) obtained previously, Cr(2-ethylhecanoate)$_3$ (a) and 1,1,2,2-tetrachloroethane (d) were added sequentially according to the ratio of a:b:c:d=1:0.5:300:1. The reaction was conducted at room temperature for 10 minutes, and then the product was removed for further application.

3. Ethylene Oligomerization

Referring to table 1, a 500 mL autoclave was heated to be vacuated for 2 hours. After being substituted with nitrogen gas several times, the autoclave was charged with ethylene. The temperature was reduced to a predetermined temperature, then dehydrated toluene (200 mL) and the catalyst produced previously was added. Oligomerization was conducted at 40° C., 5.0 MPa. After 30 minutes reaction, the temperature was lowed by ice bath and the pressure was removed. The reaction was terminated with 10% by mass of acidified ethanol. The oligomer obtained was 22.8 g. The activity of the catalyst was $2.13 \times 10^6$ g oligomer/mol Cr.h.

EXAMPLE 2

1. Preparation of N-cyclopentylbis(diphenylphosphino) ligand

Dehydrated dichloromethane (20 mL), triethylamine (3.75 mL) and diphenyl phosphorus chloride (1.326 mL, 7.2 mmol) were added to a 100 mL reactor equipped with agitator and substituted with $N_2$ completely. The temperature was reduced to 0° C. Cyclopentylamine (0.415 ml, 3.5 mmol) was added gradually. The reaction system was agitated for 30 min, and then heated to room temperature to keep reaction for another 12 hours. The product was obtained by filtering and drying (0.55 g, 32.68%).

2. Preparation of the Catalyst

Dehydrated cyclohexane (10 mL) was added to a 100 mL reactor equipped with agitator and substituted with $N_2$ completely. Then 1.4 mol/L of solution of methylaluminoxane in toluene (c), (diphenyl)phosphorous-nitrogen (cyclopentyl) phosphorous(diphenyl) ligand N-cyclopentylbis(diphenylphosphino) (b) obtained previously, tetrahydrofuran chromium chloride (a) and 1,1,2,2-tetrabromoethane (d) were added sequentially according to the ratio of a:b:c:d=1:0.5:50:0.5. The reaction was conducted at room temperature for 5 minutes, then the product was removed for further application.

3. Ethylene Oligomerization

Referring to table 1, a 500 mL autoclave was heated to be vacuated for 2 h. After being substituted with nitrogen gas several times, the autoclave was charged with ethylene. The temperature was reduced to a predetermined temperature, and then dehydrated cyclohexane (200 mL) and the catalyst produced previously were added. Oligomerization was conducted at 30° C., 6.0 MPa. After 20 minutes reaction, the temperature was lowed by ice bath and the pressure was removed. The reaction was terminated with 10% by mass of acidified ethanol. The oligomer obtained was 49.4 g. The activity of the catalyst was $1.70 \times 10^6$ g oligomer/mol Cr.h.

EXAMPLE 3

1. Preparation of (diphenyl)phosphrous-nitrogen(fluorenyl) phosphorous(diphenyl) ligand Dehydrated dichloromethane (20 mL), triethylamine (3.75 mL) and diphenyl phosphorus chloride (1.326 mL, 7.2 mol) were added to a 100 mL reactor equipped with agitator and substituted with $N_2$ completely. The temperature was reduced to 0° C. Fluorenamine (0.652 g, 3.6 mmol) was added gradually. The reaction system was agitated for 30 min, and then heated to room temperature to keep reaction for another 12 hours. The product was obtained by Filtering and drying (0.48 g, 24.3%).

2. Preparation of the Catalyst

Dehydrated cyclohexane (10 mL) was added to a 100 mL reactor equipped with agitator and substituted with $N_2$ completely. Then Propyl aluminoxane (c), (diphenyl)phosphorous-nitrogen (fluorenyl) phosphorous(diphenyl) ligand (b) obtained previously, acetylactone chromium (a) and 1,2-dimethoxyl ethane (d) were added sequentially according to the ratio of a:b:c:d=1:1:200:3. The reaction was conducted at room temperature for 5 minutes, then the product was removed for further application.

3. Ethylene Oligomerization

Referring to table 1, a 500 mL autoclave was heated to be vacuated for 2 h. After being substituted with nitrogen gas several times, the autoclave was charged with ethylene. The temperature was reduced to a predetermined temperature, then dehydrated benzene (200 mL) and the catalyst produced previously were added. Oligomerization was conducted at 200° C., 2.0 MPa. After 40 minutes reaction, the temperature was lowed by ice bath and the pressure was removed. The reaction was terminated with 10% by mass of acidified ethanol. The oligomer obtained was 47.9 g. The activity of the catalyst was $1.64 \times 10^6$ g oligomer/mol Cr.h.

EXAMPLE 4

1. Preparation of 1,4-di(N(P(phenyl)$_2$)$_2$)-benzene ligand

Dehydrated dichloromethane (20 mL), triethylamine (3.75 mL) and diphenyl phosphorus chloride (1.326 mL, 7.2 mmol) were added to a 100 mL reactor equipped with agitator and substituted with $N_2$ completely. The temperature was reduced to 0° C. 1,4-phenylenediamine (0.19 g, 1.8 mmol) was added gradually. The reaction system was agitated for 30 min, and then heated to room temperature to keep reaction for another 12 hours. The product was obtained by filtering and drying (0.8 g, 52.3%).

2. Preparation of the Catalyst

Dehydrated cyclohexane (10 mL) was added to a 100 mL reactor equipped with agitator and substituted with $N_2$ completely. Then 1.4 mol/L of solution of methyl aluminoxane in toluene (c), 1,4-di(N(P(phenyl)$_2$)$_2$)-benzene ligand (b) obtained previously, Cr(2-ethylhecanoate)$_3$ (a) and 1,2-dichloroethane (d) were added sequentially according to the ratio of a:b:c:d=1:10:300:10. The reaction was conducted at room temperature for 10 minutes, then the product was removed for further application.

3. Ethylene Oligomerization

A 500 mL autoclave was heated to be vacuated for two hours. After being substituted with nitrogen gas several times, the autoclave was charged with ethylene. The temperature was reduced to a predetermined temperature, then dehydrated heptane (200 mL) and the catalyst produced previously were added. Oligomerization was conducted at 90° C., 7.0 MPa. After 20 minutes reaction, the temperature was lowed by ice bath and the pressure was removed. The reaction was terminated with 10% by mass of acidified ethanol. The activity of the catalyst was $8.23 \times 10^6$ g oligomer/mol Cr.h. The distribution of oligomerization product is shown in table 1.

EXAMPLE 5

1. Preparation of (diphenyl)phosphorous-nitrogen(cyclohexyl)phosphorous(diphenyl) ligand Dehydrated dichloromethane (20 mL), cyclohexyamine (3.75 mL) and diphenyl phosphorus chloride (1.326 mL, 7.2 mmol) were added to a 100 mL reactor equipped with agitator and substituted with $N_2$ completely. The temperature was reduced to 0° C. 1,4-phenylenediamine (0.19 g, 1.8 mmol) was added gradually. The reaction system was agitated for 30 min, and then heated to room temperature to keep reaction for another 12 hours. The product was obtained by filtering and drying (0.8 g, 52.3%).

2. Preparation of the Catalyst

Dehydrated xylene (10 mL) was added to a 100 mL reactor equipped with agitator and substituted with $N_2$ completely. Then 1.4mol/L of solution of methylaluminoxane in toluene (c), (diphenyl)phosphorous-nitrogen (cyclohexyl)phosphorous(diphenyl) ligand (b) obtained previously, tetrahydrofuran chromium chloride (a) and 1,4-dichlorobenzene (d) were added sequentially according to the ratio of a:b:c:d=1:5:2000:8. The reaction was conducted at room temperature for 5 minutes, then the product was removed for further application.

3. Ethylene Oligomerization

A 500 mL autoclave was heated to be vacuated for two hours. After being substituted with nitrogen gas several times, the autoclave was charged with ethylene. The temperature was reduced to a predetermined temperature, then dehydrated xylene (200 mL) and the catalyst produced previously were added. Oligomerization was conducted at 150° C., 5.0 MPa. After 50 minutes reaction, the temperature was lowed by ice bath and the pressure was removed. The reaction was terminated with 10% by mass of acidified ethanol. The oligomer obtained was 24.1 g. The activity of the catalyst was $2.28 \times 10^6$ g oligomer/mol Cr.h. The distribution of oligomerization product is shown in table 1.

EXAMPLE 6

1. Preparation of (diphenyl)phosphrous-nitrogen(isopropyl)phosphorous(diphenyl) ligand Dehydrated dichloromethane (20 mL), isopropylamine (5.5 mL) and diphenyl phosphorus chloride (1.326 mL, 7.2 mmol) were added to a 100 mL reactor equipped with agitator and substituted with $N_2$ completely. The temperature was reduced to 0° C. 1,4-phenylenediamine (0.19 g, 1.8 mmol) was added gradually. The reaction system was agitated for 30 min, and then heated to room temperature to keep reaction for another 12 hours. The product b was obtained by filtering and drying (0.8 g, 52.3%).

2. Ethylene Oligomerization

A 500 mL autoclave was heated to be vacuated for 2 h. After being substituted with nitrogen gas several times, the autoclave was charged with ethylene. The temperature was reduced to a predetermined temperature, then dehydrated isopropyl benzene (200 mL) was added. Then 1.4 mol/L of solution of methyl aluminoxane in toluene (c), (diphenyl)phosphorous-nitrogen(isopropyl)phosphorous(diphenyl) (b) obtained previously, tetrahydrofuran chromium chloride (a) and 1,4-dichlorobenzene (d) were added sequentially according to the ratio of a:b:c:d=1:2:300:3. Oligomerization was conducted at 50° C., 7.0 MPa. After 30 minutes reaction, the temperature was lowed by ice bath and the pressure was removed. The reaction was terminated with 10% by mass of acidified ethanol. The oligomer obtained was 6.32 g. The activity of the catalyst was $2.30 \times 10^6$ g oligomer/mol Cr.h. As is shown in table 1.

EXAMPLE 7

1. Preparation of (dinaphthyl)phosphorous-nitrogen(butyl)phosphorous(dinaphthyl) ligand Dehydrated dichloromethane (20 mL), isopropylamine (5.5 mL) and diphenyl phosphorus chloride (1.326 mL, 7.2 mmol) were added to 100 mL reactor equipped with agitator and substituted with $N_2$ completely. The temperature was reduced to 0° C. 1,4-phenylenediamine (0.19 g, 1.8 mmol) was added gradually. The reaction system was agitated for 30 min, and then heated to room temperature to keep reaction for another 12 hours. The product was obtained by filtering and drying (0.8 g, 52.3%).

2. Ethylene Oligomerization

A 500 mL autoclave was heated to be vacuated for 2 h. After being substituted with nitrogen several times, the autoclave was charged with ethylene. The temperature was reduced to a predetermined temperature, and then dehydrated cyclohexane (200 mL) was added. The 1.4 mol/L of solution of methylaluminoxane in toluene (c), (diphenyl) phosphorous-nitrogen(butyl)phosphorous(diphenyl) (b) obtained previously, tetrahydrofuran chromium chloride (a) and 1,1,2,2-tetrafluoroethane(d) were added sequentially according to the ratio of a:b:c:d=1:1:200:3. Oligomerization was conducted at 50° C., 8.0 MPa. After 20 minutes reaction, the temperature was lowed by ice bath and the pressure was removed. The reaction was terminated with 10% by mass of acidified ethanol. The oligomer obtained was 43.2 g. The activity of the catalyst was $1.51 \times 10^6$ g oligomer/mol h. As is shown in table 1.

TABLE 1

|  | Example 1 | Example 2 | Example 3 | Example 4 | Example 5 | Example 6 | Example 7 |
|---|---|---|---|---|---|---|---|
| Activity of catalyst (g oligomer/mol Cr · h) × $10^6$ | 2.13 | 1.70 | 2.64 | 8.23 | 2.28 | 2.30 | 1.51 |
| Selectivity to 1-$C_4^=$ (wt %) | 0.54 | 0.32 | 0.73 | 0.45 | 0.01 | 0.69 | 0.73 |
| Selectivity to 1-$C_6^=$ (wt %) | 11.03 | 12.52 | 18.31 | 19.40 | 33.81 | 21.65 | 21.82 |
| Selectivity to 1-$C_8^=$ (wt %) | 73.40 | 71.13 | 70.15 | 75.84 | 69.34. | 70.20 | 72.06 |
| Purity [a] to 1-$C_8^=$ (%) | 99.24 | 98.70 | 98.71 | 98.81 | 96.07 | 96.03 | 98.01 |
| Polymer | 0.2% | 0.1% | 0.2% | 0.1% | 0.1% | 0.02% | 0.06% |

[a] refers to the percentage of 1-$C_8^=$ in $C_8$.

What is claimed is:

1. A catalyst composition for ethylene oligomerization, the composition comprising a chromium compound, ligands containing P and N, an activator and accelerator, wherein the chromium compound is selected from the group consisting of acetyl acetone chromium, THF-chromium chloride and Cr(2-ethylhecanoate)$_3$; the general formula of the ligand containing P and N is shown as:

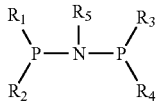

in which $R_1$, $R_2$, $R_3$ and $R_4$ are phenyl, benzyl, fluorenyl or naphthyl, $R_5$ is isopropyl, butyl, cyclopropyl, cyclopentyl, cyclohexyl or fluorenyl;
the activator is selected from the group consisting of methylaluminoxane, ethylaluminoxane, propylaluminoxane and butylaluminoxane;
the accelerator is selected from the group consisting of 1,1,2,2-tetrachloroethane, 1,1,2,2-tetrabromoethane, 1,1,2,2,-tetrafluoroethane and compounds having a formula of $X_1R_6X_2$, in which $X_1$ and $X_2$ are F, Cl, Br, I or alkoxyl, $R_6$ is alkylene or arylene group; and
the molar ratio of the chromium compound:the ligand containing P and N:the activator:the accelerator is 1:0.5-10:50-3000:0.5-10.

2. A process for the preparation of a catalyst composition for ethylene oligomerization, including mixing an activator, a ligand containing P and N, a chromium compound, and an accelerator in an inert solvent sequentially under nitrogen condition and making them to react, wherein the molar ratio of the chromium compound, the ligand containing P and N, the activator, and the accelerator is 1:0.5-10:50-3000:0.5-10.

3. The process according to claim 2, wherein in the inert solvent includes cyclohexane, xylene, or isopropylbenzene.

4. A process for ethylene oligomerization in the presence of the catalyst composition of claim 1 comprising the steps of:
mixing the chromium compound, the ligand containing P and N, the activator and the accelerator under nitrogen atmosphere for at least 10 minutes to provide an intermediate, wherein the molar ratio between the chromium compound, the ligand containing P and N, the activator, and the accelerator is 1:0.5-10:50-3000:0.5-10;
incorporating the intermediate into a reactor;
introducing ethylene for oligomerization;
wherein the reaction takes place in a inert solvent, and the inert solvent includes alkane, arene, halohydrocarbon or alkene, the reaction temperature is between 30° C. and 200° C., the pressure is between 0.5 MPa and 20.0 MPa and the reaction time is between 0.1 hour and 2 hours.

5. The process according to claim 4, wherein the chromium compound, the ligand containing P and N, the activator and the accelerator are directly added to the reactor respectively, and ethylene is introduced for oligomerization.

6. The process according to claim 4, wherein in the oligomerization, the reaction temperature is between 20° C. and 90° C., the reaction pressure is between 1 MPa and 10 MPa and the reaction time is between 0.3 hour and 1 hour.

7. The process according to claim 4, wherein in the oligomerization, the reaction temperature is between 30° C. and 70° C., the reaction pressure is between 2 MPa and 6 MPa and the reaction time is between 0.5 hour and 0.7 hour.

8. The process according to any one of claims 4-7, wherein the oligomerization is carried out in inert solvent, wherein the solvent comprises benzene, toluene, dimethylbenzene, isopropylbenzene, n-heptane, n-hexane, methylcyclohexane, cyclohexane, 1-hexene, 1-octene or ionic liquid.

* * * * *